United States Patent [19]
Bergman et al.

[11] Patent Number: 5,438,061
[45] Date of Patent: Aug. 1, 1995

[54] 7-SUBSTITUTED-δ4-6-AZASTEROID DERIVATIVES AS 5α-REDUCTASE INHIBITORS

[75] Inventors: Jeffrey P. Bergman, Ridgefield Park; Donald W. Graham, Mountainside; Gary H. Rasmusson, Watchung; Richard L. Tolman, Warren; Derek Von Langen, Fanwood, all of N.J.

[73] Assignee: Merck & Co., Inc., Rahway, N.J.

[21] Appl. No.: 93,107

[22] Filed: Jul. 16, 1993

[51] Int. Cl.$^6$ .................. C07D 221/18; A61K 31/44
[52] U.S. Cl. ..................................... 514/284; 546/61
[58] Field of Search ........................ 546/61; 514/284

[56] References Cited

U.S. PATENT DOCUMENTS

| | | | |
|---|---|---|---|
| 4,377,584 | 3/1983 | Rasmusson et al. | 424/258 |
| 4,760,071 | 7/1988 | Rasmusson et al. | 514/284 |
| 4,859,681 | 8/1989 | Rasmusson et al. | 514/284 |
| 5,049,562 | 9/1991 | Rasmusson et al. | 514/284 |

FOREIGN PATENT DOCUMENTS

| | | |
|---|---|---|
| 0004949 | 10/1979 | European Pat. Off. . |
| 0155096 | 9/1985 | European Pat. Off. . |
| 0314199 | 5/1989 | European Pat. Off. . |
| WO93/13124 | 8/1993 | WIPO . |
| WO93/23419 | 11/1993 | WIPO . |
| WO93/23420 | 11/1993 | WIPO . |

OTHER PUBLICATIONS

Frye et al., Chemical Abstracts, vol. 199, (25)abst. 119:271,484J Dec. 20, 1993 Abstracting PCT Int. Appl. WO-93-13,124 Pub. 8 Jul. 1993.
Brooks, et al., "Prostatic Effects Induced in Dogs by Chronic or Acute Oral Adminstration . . . ", The Prostate, vol. 9, pp. 65-75 (1986).
Kadohama, et al., "Retardation of Prostate Tumor Progression in Nobel Rat . . . ", J NCL, vol. 74, No. 2, pp. 475-486 (1985).
Bingham, et al., "The Metabolism of Testosterone By Human Male Scalp Skin", J. Endocr. (England), vol. 57, pp. 111-121 (1973).
Brooks, et al., "5 Alpha Reductase Inhibitory and Anti--Androgenic Activities . . . ", Steroids, vol. 47, pp. 1-19 (1986).
Rasmusson, et al., "Azasteroids: Structure-Activity Relationships for Ihibition . . . ", J. Med. Chem., vol. 29, pp. 2298-2315 (1986).
Rasmusson, et al., "Azasteroids as Inhibitors of Rat Prostatic 5-Alpha Reductase", J. Med. Chem., vol. 27, pp. 1690-1701 (1984).
Rittmaster, et al., "the Effects of N,N-Diethyl-4-Methyl-3-Oxo-4-Aza-5-Alpha Androstane . . . ", J. Clin. Endo. 7 Metab., vol. 65, pp. 188-193 (1987).
Metcalf, et al., "Inhibitors of Steroid 5 Alphas Reductase in Benign . . . ", TIPS, vol. 10, pp. 491-495 (1989).
Diani, et al., "Hair Growth Effects of Oral Administra-
(List continued on next page.)

*Primary Examiner*—Alan L. Rotman
*Attorney, Agent, or Firm*—Catherine D. Fitch; Carol S. Quagliato; Melvin Winokur

[57] ABSTRACT

Compounds of the formula I

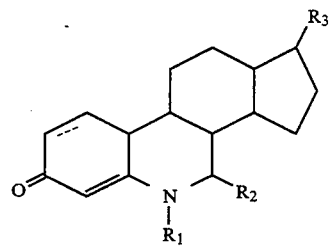

wherein $R_1$ hydrogen or methyl; $R_2$ is methyl; $R_3$ hydrogen, Alk-$R_4$, X-Alk, $C_{1-6}$-X-Alk, XCO-Alk, CN, CO-Alk, CO-Ar, CO-O-Alk, CO-NH-Alk, CO-NH-Ar, CO-NH-Het and CO-N(Alk)$_2$; Alk is $C_{1-12}$ straight or branched alkyl; Ar is phenyl, Het is piperidinyl, piperizinyl, pyrrolidinyl, pyrrolyl, furanyl or thienyl and X is O, N or S. Such compounds are useful in the treatment of pathologic conditions that benefit from blockade of isozymes of 5α-reductase.

4 Claims, No Drawings

OTHER PUBLICATIONS tion of Finasteride, a Steroid . . . ", J. Clin. Endo. & Metab., vol. 74, pp. 345–350 (1992).

Gormley, et al., "Role of 5 Alpha Reductase Inhibitors in Treatment of Advanced Prostatic Carcinoma", Urol. Clinics of N. Amer., vol. 18, pp. 93–98 (1991).

Gormley, et al., "Effect of Finasteride on Serum PSA Levels in Men w/Prostate Cancer", 2nd Intnl. (Jan. 18, 1992).

Stinson, "Prostate Drug Proscar Cleared for Marketing", Chemical Engineering News, pp. 7–8, (29 Jun. 1992).

7-SUBSTITUTED-δ4-6-AZASTEROID DERIVATIVES AS 5α-REDUCTASE INHIBITORS

FIELD OF THE INVENTION

The present invention provides novel compounds, novel compositions, methods of their use and methods of their manufacture, where such compounds are generally pharmacologically useful as agents in therapies whose mechanism of action rely on the selective inhibition of the isozyme 5α reductase 1.

BACKGROUND OF THE INVENTION

Certain undesirable physiological manifestations, such as acne vulgaris, seborrhea, female hirsutism, male pattern baldness (alopecia) and benign prostatic hyperplasia, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neff, et al., *Endocrinol.* 1972, 91 (2). However, these products though devoid of hormonal effects, compete with all natural androgens for receptor sites, and hence have a tendency to feminize a male host or the male fetus of a female host and/or initiate feedback effects which would cause hyperstimulation of the testes.

The principal mediator of androgenic activity in some target organs, e.g. the prostate, is 5α-dihydrotestosterone, formed locally in the target organ by the action of testosterone-5α-reductase. Inhibitors of testosterone-5α-reductase will serve to prevent or lessen symptoms of hyperandrogenic stimulation in these organs. It is now known that a second 5α-reductase isozyme exists, which interacts with epidermal tissues, especially in scalp tissues. This form is conventionally designated as 5α-reductase 1, while the isozyme that principally interacts with the prostatic tissues is designated as 5α-reductase 2. Both isozymes are active, to differing extents, in the prostatic tissues. In the treatment of hyperandrogenic disease conditions e.g. benign prostatic hyperplasia (BPH), it would be desirable to have one drug entity which is active against both isozymes in the prostate to significantly inhibit dihydrotesterone production, while also having another drug entity which is highly selective for inhibiting the isozyme 5α-reductase 1 associated with the scalp, for use in treating conditions of the skin and scalp, e.g. acne and alopecia in males and hirsutism in females. Additionally, such a selective 5α-reductase 1 inhibitor could also be used in combination with finasteride (PROSCAR®), which is highly selective for 5α-reductase 2, for combination therapy in the treatment of BPH. Therefore, it is an object of this invention to provide compounds that have sufficient activity in the inhibition of one or both 5α-reductase isozymes. It is an additional object of this invention to provide compounds that are useful in the treatment and/or prevention of benign prostatic hyperplasia. It is an additional object of this invention to provide compounds that are useful in the treatment of female hirsutism, male pattern baldness, acne, androgenetic alopecia, prostatic cancer, and insufficient plasma levels of high density lipoproteins. The compounds of the invention have utility in one or more of the aforementioned areas.

SUMMARY OF THE INVENTION

The compounds of the present invention are those of the general structural formula I:

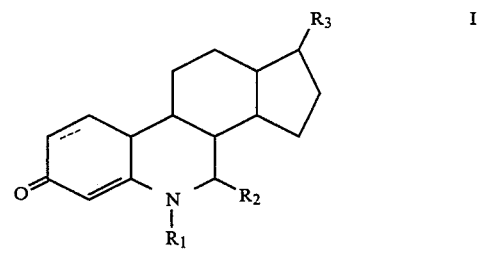

or a pharmaceutically acceptable salt or ester thereof, wherein $R_1$ is selected from the group consisting of hydrogen and methyl;

$R_2$ is methyl;

$R_3$ is selected from the group consisting of hydrogen, Alk-$R_4$, X-Alk, $C_{1-6}$-X-Alk, XCO-Alk, CN, CO-Alk, CO-Ar, CO-O-Alk, CO-NH-Alk, CO-NH-Ar, CO-NH-Het and CO-N(Alk)$_2$;

Alk is $C_{1-12}$ straight or branched alkyl;

Ar is phenyl

Het is selected from the group consisting of piperidinyl, piperizinyl, pyrrolidinyl, pyrrolyl, furanyl and thienyl;

X is selected from the group consisting of O, N and S.

DETAILED DESCRIPTION OF THE INVENTION

Salts encompassed within the term "pharmaceutically acceptable esters and salts" refer to non-toxic esters and salts of the compounds of this invention which are generally prepared by reacting the free base with a suitable organic or inorganic acid. Representative salts and esters include the following:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine ammonium salt |
| Citrate | |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |

| | |
|---|---|
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any specified numbers within this range.

Whenever the term "alkyl" or "aryl" or their prefix root appears in a name of a substituent (e.g. aralkoxyaryloxy) it shall be interpreted as including those limitations given above for "alkyl" or "aryl".

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0 and 50.0 mg of active ingredient. Effective plasma levels of the compounds of the present invention range from 0.002 mg to 50 mg per kg of body weight per day. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen. Other preferred topical preparations include creams, ointments, lotions, aerosol sprays and gels, wherein the concentration of active ingredient would range from 0.1% to 15%, w/w or w/v.

In the methods of the present invention, the compounds herein described in detail can form the active ingredient, and are typically administered in admixture with suitable pharmaceutical diluents, excipients or carders (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carder such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug carders. Such polymers can include polyvinylpyrrolidone, pyran copolymer, polyhydroxypropyl-methacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyfic acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

Synthesis Scheme I

β-homo-6-aza-steroids

-continued
Synthesis Scheme I
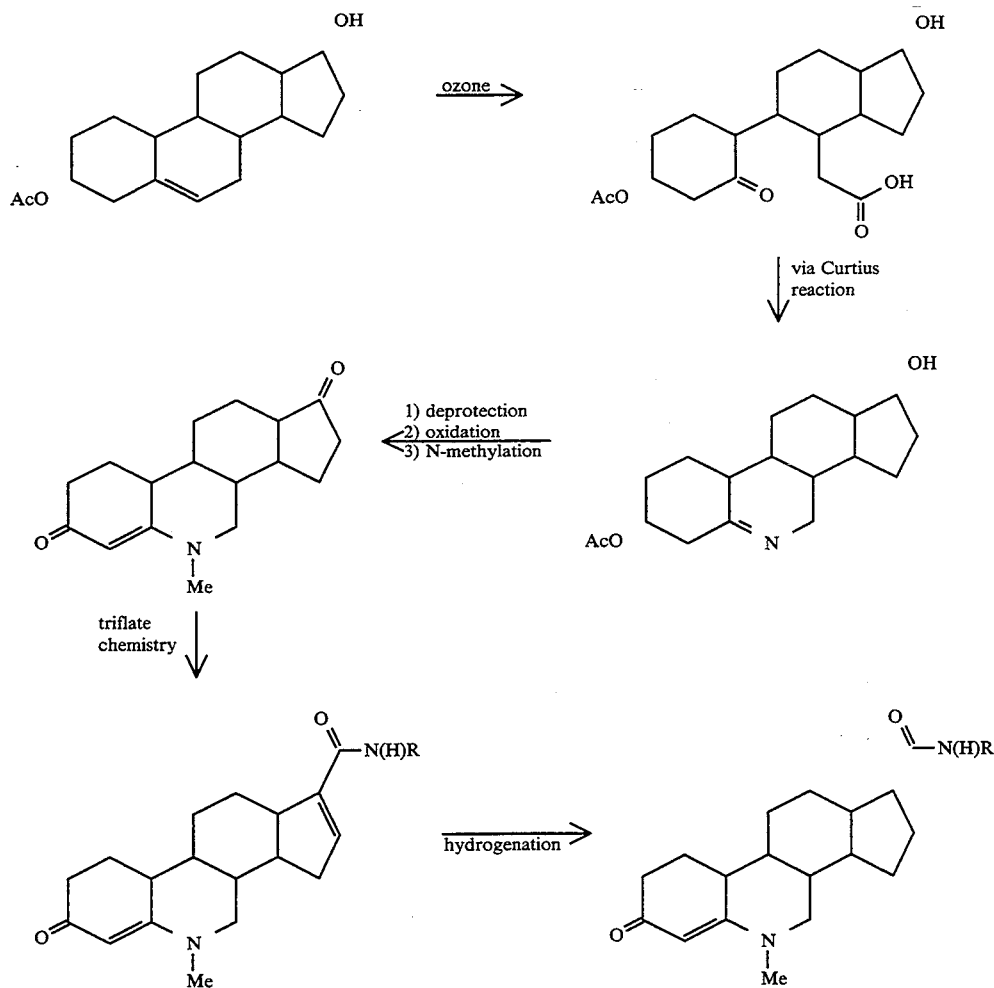
Synthesis Scheme II
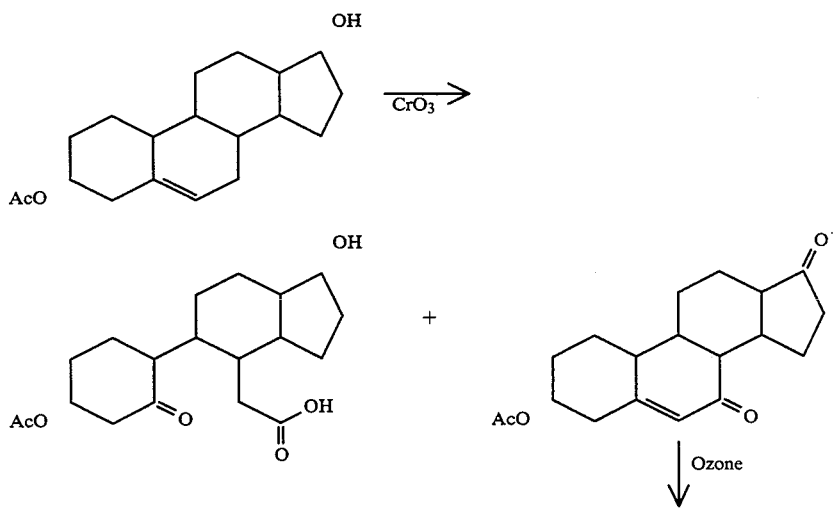

5,438,061
7 8
-continued
Synthesis Scheme II
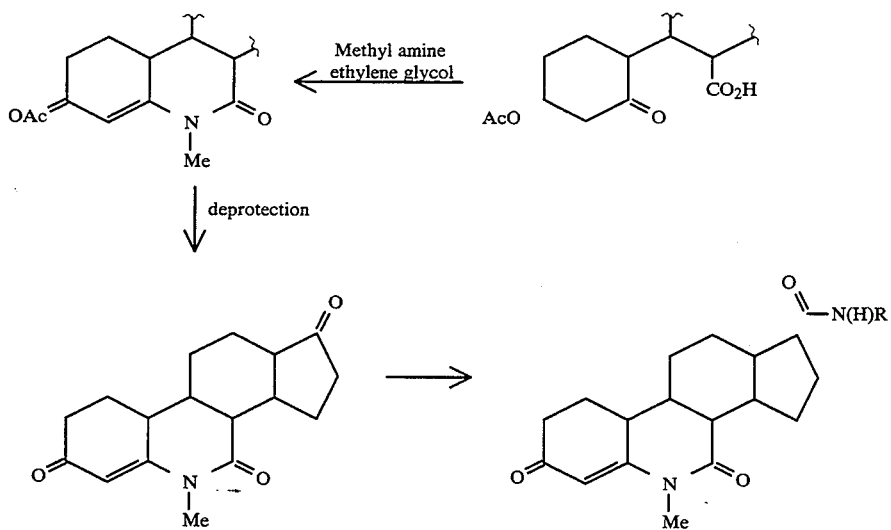
Synthesis Scheme III
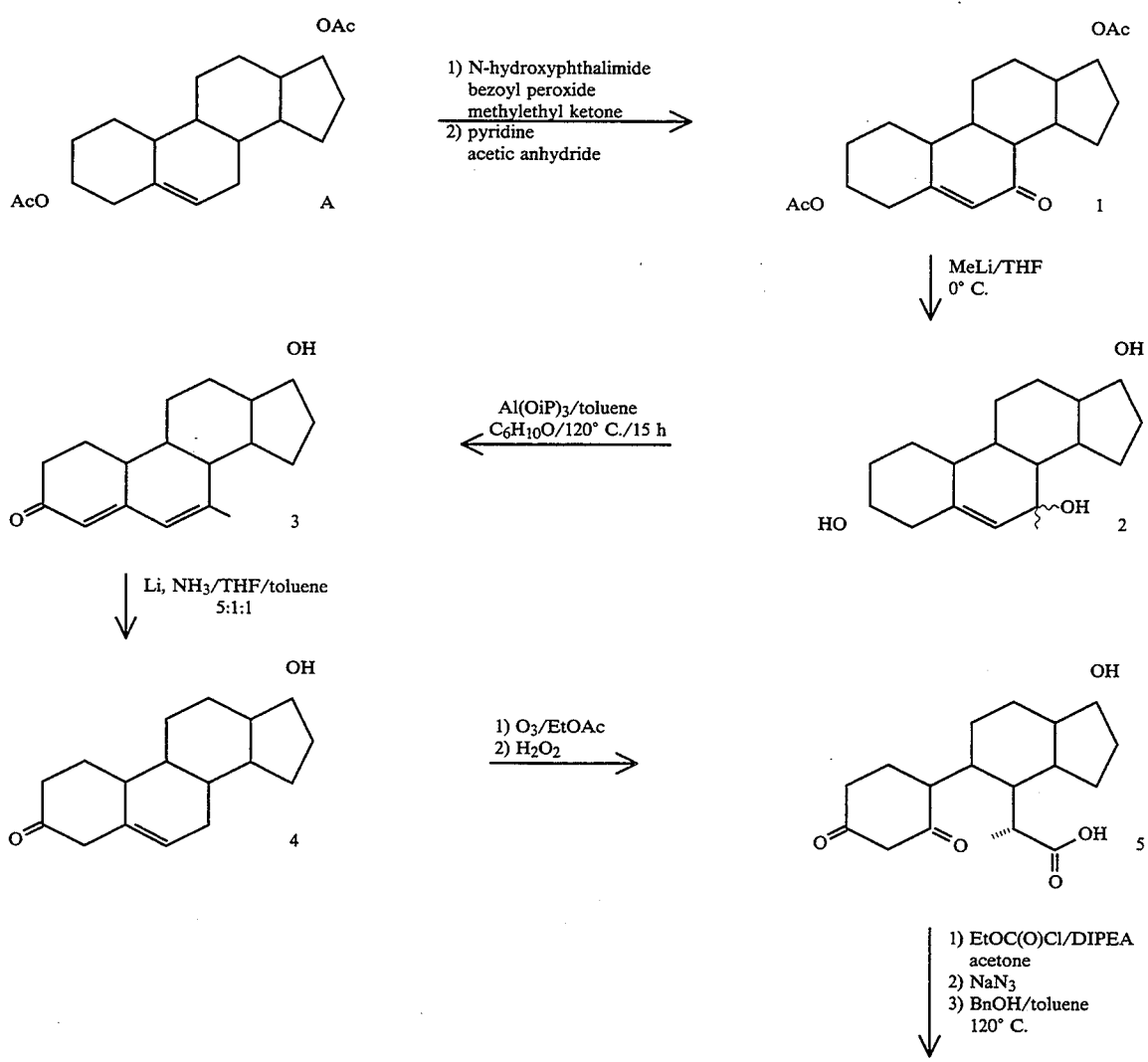

-continued
Synthesis Scheme III

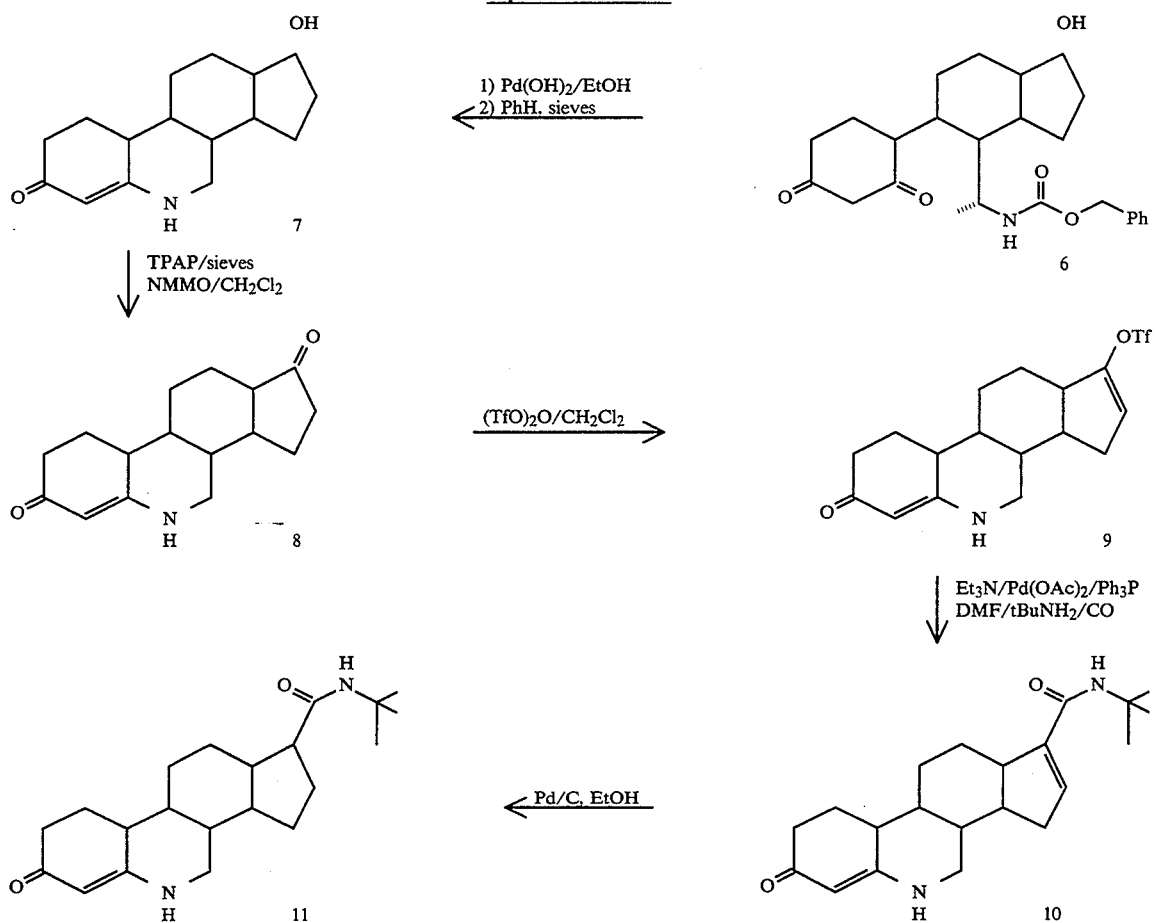

EXAMPLE 1

A solution of the known bis-acetate A (available from Sigma Chemical Company, Milwauke, Wis.), methyl-ethyl ketone, n-hydroxyphthalimide (1.1 eq), benzoyl peroxide (5 mol %) is warmed to 60° C. while a stream of air is slowly bubbled through the yellow reaction mixture. After 5 hours the reaction is cooled and concentrated. The concentrate is slurried in dichloromethane and filtered. The filtrate is then concentrated, disolved in pyridine and chilled to 0° C. Acetic anhydride is added and the resulting solution stirred overnight at room temperature. The reaction is concentrated, slurried with methanol, warmed to 50° C. for 20 minutes, cooled and filtered to yield 1.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

EXAMPLE 2

The enone product of Example 1 is taken into anhydrous THF and cooled to 0° C. Methyllithium (6.5 eq, 1.5M in ether) is added dropwise and the resulting mixture stirred for 1 hour at 0° C. The reaction is quenched with 1M ammonium chloride and extracted with dichloromethane. Drying over anhydrous sodium sulfate and removal of solvent affords 2.

EXAMPLE 3

The carbinol product of Example 2 is dissolved in toluene and the resulting solution is treated with cyclohexanone and aluminum triisopropoxide and warmed to 120° C. for 15 hours. The reaction is then cooled to ambient temperature and quenched with water. Extraction with dichloromethane, drying over anhydrous sodium sulfate and removal of volatiles gives 3.

EXAMPLE 4

The dienone product of Example 3 is taken into a −50° C. mixture of ammonia:THF:toluene (5:1:1) and treated with excess lithium metal for two hours. The excess lithium is then decomposed with 1,2-dibromoethane and the enolate quenched with ammonium chloride. The reaction is warmed to room temperature to remove the ammonia and diluted with more toluene. This mixture is washed with water then brine, and dried over anhydrous sodium sulfate. Removal of solvent gives the olefin 4.

EXAMPLE 5

The olefin product of Example 4 is dissolved in ethyl acetate and cooled to −20° C. and ozone is bubbled through the solution for 3 hours. The blue solution is warmed to room temperature and treated with excess 30% hydrogen peroxide and vigorously stirred for 48 hours longer. The reaction is washed with water and concentrated to remove the ethyl acetate. The residue is partitioned between ether and 2N sodium hydroxide. The ether is extracted with 2N sodium hydroxide once more and the basic extracts combined. Dichloromethane is added to the aqueous base and the biphasic mixture cooled to 0° C. and acidified to pH 2 with 2N sulfuric acid. The phases are separated and the aqueous extracted twice more with dichloromethane. After washing with brine, the combined organic extracts are dried over anhydrous sodium sulfate and concentrated to afford the acid 5.

EXAMPLE 6

The acid product of Example 5 is dissolved in anhydrous acetone and diisopropylethylamine (1.5 eq) is added. The solution is cooled to 0° C. and treated with ethyl chloroformate (1 eq) dropwise. After stirring for 2 hours the mixture is treated, dropwise, with sodium azide (2 eq) dissolved in a minimal amount of water. After stirring an additional hour, the reaction is quenched with ice water and extracted with toluene (×6), dried over anhydrous sodium sulfate and concentrated to ¼ original volume. This concentrate is added to a 100° C. solution of benzyl alcohol (5 eq) in toluene and stirred for 15 min. or until gas evolution ceases. The reaction temperature is raised to reflux and stirring is continued for an additional 3 hours. The reaction is cooled and concentrated to afford the benzyl carbamate 6.

EXAMPLE 7

The carbamate product of Example 6 is dissolved in ethanol and palladium hydroxide (10 wt %) is added. The resulting black suspension is stirred under a hydrogen balloon for 24 hours, filtered to remove the catalyst and concentrated. The residue is dissolved in benzene and crushed 3 angstrom sieves are added. Stirring is continued for 16 hours and the mixture is filtered and concentrated to afford the vinylogous amide 7.

EXAMPLE 8

The vinylogous amide product of Example 7 is taken into dichloromethane and powdered 4 angstrom sieves (500 mg/g 7), N-methylmorpholine-N-oxide (1.5 eq) and TPAP (5 mol %). The green mixture is stirred for 30 minutes during which time the reaction becomes black colored. The mixture is then filtered through a small pad of silica gel eluting with ethyl acetate to yield the ketone 8.

EXAMPLE 9

The ketone product of Example 8 is dissolved in anhydrous dichloromethane chilled to 0° C. and treated with triflic anhydride (2.2 eq). After stirring for 2 hours the reaction is diluted with water and extracted with more dichloromethane. After washing with brine and drying over anhydrous sodium sulfate, the solvent is removed to afford triflate 9.

EXAMPLE 10

A solution of the triflate product of Example 9, triethylamine (2 eq), palladium acetate (0.03 eq), triphenylphosphine (0.06 eq), t-butylamine (40 eq) and DMF is purged with carbon monoxide for 5 minutes and then stirred under a balloon of CO for 24 hours. Ethyl acetate and water is added to the reaction, the phases separated and the water extracted once more with ethyl acetate. The combined organic solutions are washed with brine, dried over anhydrous sodium sulfate and concentrated to yield the amide 10.

EXAMPLE 11

The amide product of Example 10 is dissolved in ethanol and palladium hydroxide (10 mol %) is added. The resulting black suspension is stirred under a hydrogen balloon for 20 hours. The mixture is filtered and concentrated to give 11.

BIOLOGICAL ASSAYS

5α-reductase assay.

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C-T (or $^3$H-T), 1 mM DTT, and 500 μM NADPH. Typically, the assay is initiated by the addition of 50–100 μg prostatic homogenate or 75–200 μg scalp homogenate and incubated at 37° C. After 10–50 min the reaction is quenched by extraction with 250 μl of a mixture of 70% cyclohexane: 30% ethyl acetate containing 10 μg each DHT and T. The aqueous and organic layers are separated by centrifugation at 14,000 rpm in an Eppendorf microfuge. The organic layer is subjected to normal phase HPLC (10 cm Whatman partisil 5 silica column equilibrated in 1 ml/min 70 % cyclohexane: 30 % ethyl acetate; retention times DHT, 6.8–7.2 min; androstanediol, 7.6–8.0; T, 9.1–9.7 min). The HPLC system consists of a Waters Model 680 Gradient System equipped with a Hitachi Model 655A autosampler, Applied Biosystems Model 757 variable UV detector, and a Radiomatic Model A120 radio-activity analyzer. The conversion of T to DHT is monitored using the radioactivity flow detector by mixing the HPLC effluent with one volume of Flo Scint 1 (Radiomatic). Under the conditions described, the production of DHT is linear for at least 25 min. The only steroids observed with the human prostate and scalp preparations were T, DHT and androstanediol.

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A. G., *The Culture of Dermal Papilla Cells From Human Hair Follicles*, Br. J. Dermatol. 110:685–689, 1984 and Itami, S. et. al., *5α-Reductase Activity In Cultured Human Dermal Papilla Cells From Beard Compared With Reticular Dermal Fibroblasts*, J. Invest. Dermatol. 94:150–152, 1990. Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle., The crude homogenate is further homogenized by a teflon-glass homogenizer, and is used as the cell homogenate. For the study of subcellular localization of 5α-reductase, the cell homogenate is centrifuged at 800×g for 10 min to yield a crude nuclear pellet. The resultant supernatant is centrifuged at 10,000×g for 15 min to produce a crude mitochondrial pellet. The supernatant is centrifuged at 100,000×g for 60 min to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 μl of the cell homogenate, in a final volume of 100 μl. Each tube contains 50-100 μg of cellular protein. Incubation is carried out at 37° C. for 30 min. During this incubation, the reaction is proportional to the time. For the study of optimum pH, citrate buffer is used at pH 4.5-6.5, and the Tris HCl buffer at pH 7.0-9.0. The protein content is determined by the method of Lowry, et. al., *Protein Measurement With The Folin Phenol Reagent.t* J. Biol. Chem. 193:265-275, 1951.

After incubation, the reaction is stopped by adding 4 times volume of chloroform-methanol (2/1:V/V) containing 110 μg each of carder steroids. The extracted steroids are analyzed by thin-layer chromatographyl as previously described by Gomez, et. al., *In Vitro Metablosim Of Testosterone-4-$^{14}$C and α-androstene-3, 17-dione-4-$^{14}$C In Human Skin.* Biochem. 7:24-32, 1968, and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

Fuzzy Rat Acne Model

Adult fuzzy rats are a variety of rat that has stunted hair growth, brown colored seborrhea coveting their entire back skin and abnormally increased sebum production after puberty that has been demonstrataed to be due to circulating androgens. 0.1, 0.05 and 0,025% solutions of a selected 5α-reductase inhibitor of interest are prepared in a vehicle of propylene glycol, isopropanol, isopropyl myristate and water (50/30/2/18%), and is topically applied onto the backs of adult male fuzzy rats, 0.2 ml per animal daily for 4 weeks. Controls receive the vehicle alone and 5 of them are castrated. After 2 weeks seborrhea will be dose-dependently depleted and after 4 weeks bromodeoxyuridine (BrdU, 200mg/kg) is intraperitoneally injected 2 hours before sacriice. The skin tissues are incubated with EDTA (20 mM) in phosphate buffer, 1.5 hours at 37° C. The pilosebaceous unit attached to the epidermis is striped from the dermis and fixed with formalin for immuno-staining of BrdU. DNA synthesis cells showing a BrdU-positive nucleus are located in the outer glandular border. The number of S-phase cells per lobe is determined with a micro-image apparatus. Using formalin fixed skin, frozen serial sections are stained with 1% osmium and the size of the lobes is measured. A positive inhibitor of skin 5α-reductrase will induce suppression of sebum production by inhibiting the rate of glandular cell turnover, and showing reduced lobular size.

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment and prevention of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. For the treatment of androgenic alopecia, acne vulgaris, seborrhea, female hirsutism, the compounds of the present invention are administered in a pharmaceutical composition comprising the active compound in combination with a pharmacologically acceptable carder adapted for topical, oral or parenteral administration.

These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a 5α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. An ordinarily skilled physician or veterinarian can readily determine and prescribe the effective amount of the drug required to prevent, counter or arrest the progress of the condition.

Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range from about 0.01 mg. to 50 mg./kgs. of body weight per day. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carders (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carder such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carders. Such polymers can include polyvinylpyrrolidone, pyran copolymer, polyhydroxypropyl- methacrylamide-phenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carders, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula I

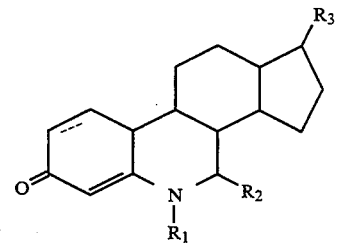

or a pharmaceutically acceptable salt thereof, wherein:

$R_1$ is selected from the group consisting of hydrogen and methyl;

$R_2$ is methyl;

$R_3$ is selected from the group consisting of hydrogen, [Alk-$R_4$,] X-Alk, $C_{1-6}$-X-Alk, XCO-Alk, and [CN, CO-Alk,] CO-Ar [,CO-O-Alk, CO-NH-Alk, CO-NH-Ar, CO-NH-Het and CO-N(Alk)$_2$];

Alk is $C_{1-12}$ straight or branched alkyl;

Ar is phenyl; and

X is selected from the group consisting of O, NH and S.

2. A method for treating, in a mammal in need thereof, the hyperandrogenic conditions of benign prostatic hyperplasia or prostatitis, comprising the step of administering to said mammal a pharmacologically effective amount of the compound as claimed in claim 1.

3. A pharmaceutical composition comprising a pharmaceutically acceptable carder and a pharmacologically effective amount of a compound as claimed in claim 1, sufficient to treat a hyperandrogenic condition in a mammal in need of such treatment.

4. A method for treating, in a mammal in need thereof, the hyperandrogenic condition of female hirsutism, comprising the step of administering to said mammal a pharmacologically effective amount of the compound as claimed in claim 1.

* * * * *

UNITED STATES PATENT AND TRADEMARK OFFICE
CERTIFICATE OF CORRECTION

PATENT NO. : 5,438,061
DATED : August 1, 1995
INVENTOR(S) : Jeffrey P. Bergman, et al It is certified that error appears in the above-indentified patent and that said Letters Patent is hereby corrected as shown below:

At Column 16, in Claim 1, at lines 45 to 48 thereof, rewrite the definition of $R_3$ to read as follows:

$R_3$ is selected from the group consisting of hydrogen, X-Alk, $C_{1-6}$-X-Alk, XCO-Alk, and CO-Ar;

Signed and Sealed this

Fifth Day of March, 1996

Attest:

BRUCE LEHMAN

*Attesting Officer*       *Commissioner of Patents and Trademarks*